United States Patent
Gallop et al.

(10) Patent No.: US 10,573,087 B2
(45) Date of Patent: Feb. 25, 2020

(54) METHOD, SYSTEM AND APPARATUS FOR RENDERING MEDICAL IMAGE DATA

(71) Applicant: SYNAPTIVE MEDICAL (BARBADOS) INC., Bridgetown (BB)

(72) Inventors: David Bruce Gallop, Toronto (CA); Kamyar Abhari, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 247 days.

(21) Appl. No.: 15/678,509

(22) Filed: Aug. 16, 2017

(65) Prior Publication Data
US 2019/0057555 A1 Feb. 21, 2019

(51) Int. Cl.
*G06T 19/20* (2011.01)
*A61B 34/20* (2016.01)
(Continued)

(52) U.S. Cl.
CPC ............ *G06T 19/20* (2013.01); *A61B 5/0042* (2013.01); *A61B 5/0082* (2013.01); *A61B 34/20* (2016.02);
(Continued)

(58) Field of Classification Search
CPC ....... G06T 19/20; G06T 15/08; G06T 7/0012; G06T 2210/41; G06T 2207/30016; G06T 2207/20092; G06T 2207/20024; G06T 2207/10088; G06T 2219/004; G06T 2219/2012; G06T 2215/16; G06T 2207/20112; G06T 2207/30004; G06T 15/00; G06T 11/008; G06T 7/10; A61B 5/0082; A61B 5/0042; A61B 90/361; A61B 34/20; A61B 2576/026; A61B 2505/05; A61B 5/4893; A61B 5/489; A61B 5/0077;
(Continued)

(56) References Cited

U.S. PATENT DOCUMENTS 5,748,801 A 5/1998 Goto
6,366,797 B1 4/2002 Fisher et al.
(Continued)

FOREIGN PATENT DOCUMENTS

WO 2001038895 A1 5/2001

OTHER PUBLICATIONS

UKIPO, Search Report under Section 17, dated Feb. 11, 2019, re UK Patent Application No. GB1813207.6.
(Continued)

*Primary Examiner* — Robert J Craddock
(74) *Attorney, Agent, or Firm* — Perry + Currier

(57) ABSTRACT

A method of rendering medical image data includes: obtaining an image, having a plurality of voxels, of a volume of patient tissue having a plurality of tissue types; for each of the plurality of voxels: determining a first type indicator value indicating a likelihood that the voxel depicts a first one of the tissue types; storing the first type indicator value in association with the voxel; setting a first type indicator threshold for the first tissue type; rendering the image on a display and applying a first visual filter to a first subset of the voxels having type indicator values that satisfy the first type indicator threshold; and updating the rendering, responsive to receiving input data specifying a modified first type indicator threshold, to apply the first visual filter to an updated first subset of the voxels having first type indicator values that satisfy the modified first type indicator threshold.

16 Claims, 9 Drawing Sheets

(51) Int. Cl.
*A61B 90/00* (2016.01)
*A61B 5/00* (2006.01)
*G06T 7/00* (2017.01)
*G06T 15/08* (2011.01)

(52) U.S. Cl.
CPC .......... *A61B 90/361* (2016.02); *G06T 7/0012* (2013.01); *G06T 15/08* (2013.01); *A61B 5/0077* (2013.01); *A61B 5/489* (2013.01); *A61B 5/4893* (2013.01); *A61B 2034/2055* (2016.02); *A61B 2034/2065* (2016.02); *A61B 2090/373* (2016.02); *A61B 2090/3945* (2016.02); *A61B 2090/3979* (2016.02); *A61B 2505/05* (2013.01); *A61B 2576/026* (2013.01); *G06T 2207/10088* (2013.01); *G06T 2207/20024* (2013.01); *G06T 2207/20092* (2013.01); *G06T 2207/30016* (2013.01); *G06T 2210/41* (2013.01)

(58) Field of Classification Search
CPC .... A61B 2090/3979; A61B 2090/3945; A61B 2090/373; A61B 2034/2065; A61B 2034/2055; A61B 5/742; A61B 2034/2051; A61B 17/3421; A61B 5/064; A61B 5/055; A61B 5/0075; A61B 5/0066; A61B 5/0033
See application file for complete search history.

(56) References Cited

U.S. PATENT DOCUMENTS

| | | | |
|---|---|---|---|
| 7,715,607 | B2 | 5/2010 | Hu et al. |
| 8,068,655 | B2 | 11/2011 | Odry et al. |
| 8,280,133 | B2 | 10/2012 | Wels et al. |
| 9,412,163 | B2 | 8/2016 | Peng et al. |
| 2005/0017972 | A1 | 1/2005 | Poole et al. |
| 2010/0074499 | A1 | 3/2010 | Wels et al. |
| 2010/0156921 | A1 | 6/2010 | McLennan et al. |
| 2010/0260396 | A1 | 10/2010 | Brandt et al. |
| 2011/0063288 | A1 | 3/2011 | Valadez |
| 2016/0110890 | A1 | 4/2016 | Smith |

OTHER PUBLICATIONS

Madan, Christopher R., Creating 3D visualizations of MRI data: A brief Guide, Version 1. F1000Res., 2015; 4: 466. Published online Aug. 4, 2015; https://www.ncbi.nlm.nih.gov/pmc/articles/PMC4648228/.

METHOD, SYSTEM AND APPARATUS FOR RENDERING MEDICAL IMAGE DATA

FIELD

The specification relates generally to medical imaging, and specifically to a method, system and apparatus for rendering medical image data.

BACKGROUND

Minimally invasive surgical techniques can reduce the risk of injury to patients, in comparison with traditional surgical techniques. The possibility for patient injury remains, however, particularly in procedures involving neural tissue, highly vascularized tissue and the like (e.g., brain and spinal surgical procedures). Current surgical planning and navigation systems may not provide sufficient information to allow accurate navigation of surgical instruments in and around sensitive tissues.

SUMMARY

An aspect of the specification provides a method of rendering medical image data including: obtaining an image of a volume of patient tissue having a plurality of tissue types; the image comprising a plurality of voxels; for each of the plurality of voxels: determining a first type indicator value indicating a likelihood that the voxel depicts a first one of the tissue types; storing the first type indicator value in association with the voxel; setting a first type indicator threshold for the first tissue type; rendering the image on a display and applying a first visual filter to a first subset of the voxels having type indicator values that satisfy the first type indicator threshold; and updating the rendering, responsive to receiving input data specifying a modified first type indicator threshold, to apply the first visual filter to an updated first subset of the voxels having first type indicator values that satisfy the modified first type indicator threshold.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
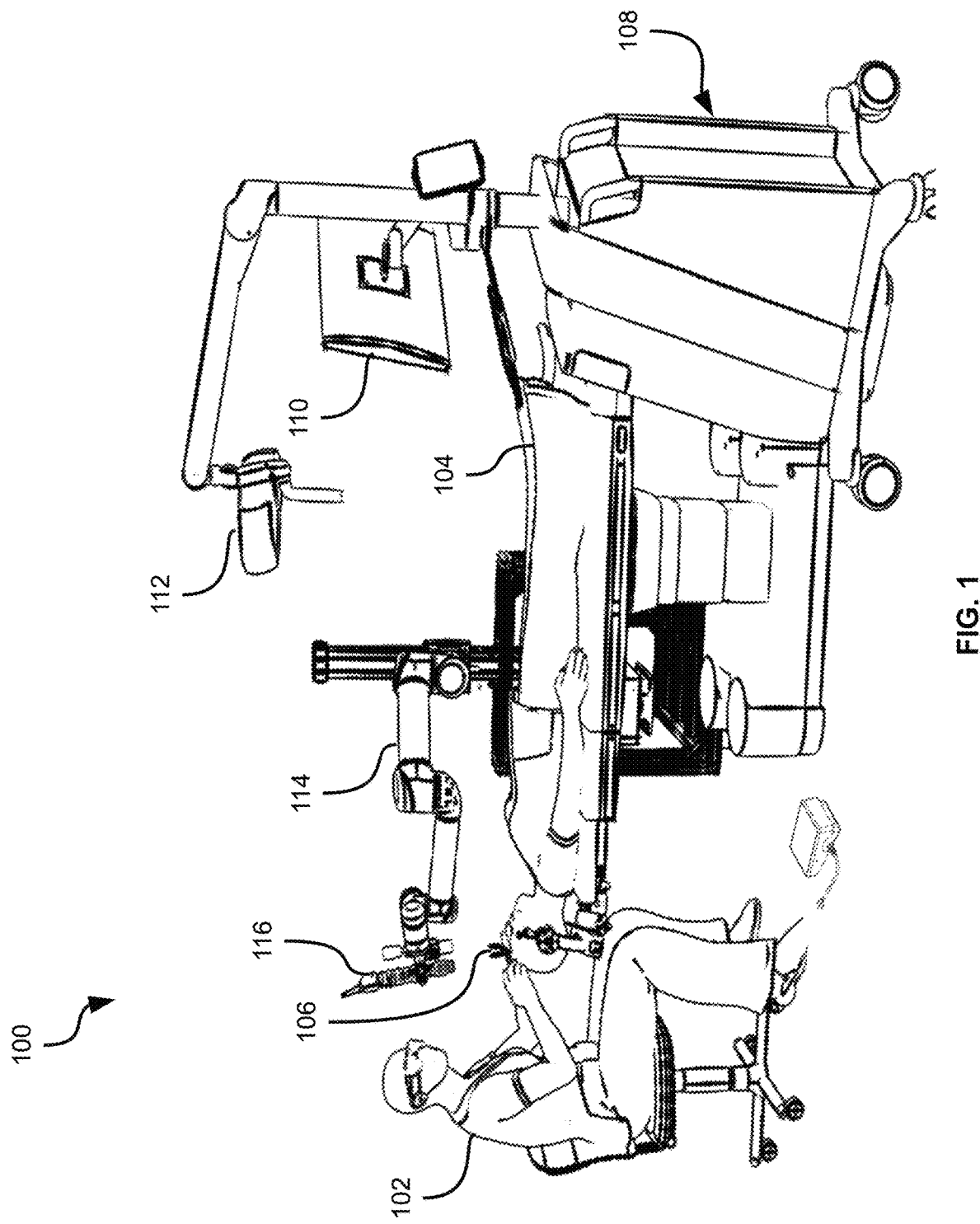
FIG. 1 depicts an operating theatre, according to a non-limiting embodiment.

FIG. 1 depicts a system 100 in the form of a surgical operating theatre in which a healthcare worker 102 (e.g. a surgeon) operates on a patient 104. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques. The description below makes reference to the brain of patient 104 as an example of tissue to which the techniques herein may be applied. It will be understood, however, that those techniques may also be applied to a wide variety of other tissues. Thus, when the brain of patient 104 is mentioned below, it is simply an example of the various tissues in connection with which the systems and methods herein may be implemented.

The opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer (not shown) is generally inserted into access port 106. The introducer is typically a cylindrical device that slidably engages the internal surface of access port 106 and bears a conical atraumatic tip to allow for insertion of access port 106 into the sulcal folds of the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like.

Also shown in FIG. 1 is an equipment tower 108 supporting a computing device (not shown) such as a desktop computer, as well as one or more displays 110 connected to the computing device for displaying images provided by the computing device.

Equipment tower 108 also supports a tracking system 112. Tracking system 112 is generally configured to track the positions of one or more reflective markers (not shown) mounted on access port 106, any of the above-mentioned surgical tools, or any combination thereof. Such markers, also referred to as fiducial markers, may also be mounted on patient 104, for example at various points on patient 104's head. Tracking system 112 may therefore include a camera (e.g. a stereo camera) and a computing device (either the same device as mentioned above or a separate device) configured to locate the fiducial markers in the images captured by the camera, and determine the spatial positions of those markers within the operating theatre. The spatial positions may be provided by tracking system 112 to the computing device in equipment tower 108 for subsequent use.

The nature of the markers and the camera are not particularly limited. For example, the camera may be sensitive to infrared (IR) light, and tracking system 112 may include one or more IR emitters (e.g. IR light emitting diodes (LEDs)) to shine IR light on the markers. In other examples, marker recognition in tracking system 112 may be based on radio frequency (RF) radiation, visible light emitted from devices such as pulsed or un-pulsed LEDs, electromagnetic radiation other than IR or visible light, and the like. For RF and EM-based tracking, each object can be fitted with markers having signatures unique to that object, and tracking system 112 can include antennae rather than the above-mentioned camera. Combinations of the above may also be employed.

Each tracked object generally includes three or more markers fixed at predefined locations on the object. The predefined locations, as well as the geometry of each tracked object, are configured within tracking system 112, and thus tracking system 112 is configured to image the operating theatre, compare the positions of any visible markers to the pre-configured geometry and marker locations, and based on the comparison, determine which tracked objects are present in the field of view of the camera, as well as what positions those objects are currently in. An example of tracking system 112 is the "Polaris" system available from Northern Digital Inc.

Also shown in FIG. 1 is an automated articulated arm 114, also referred to as a robotic arm, carrying an external scope 116 (i.e. external to patient 104). External scope 116 may be positioned over access port 106 by robotic arm 114, and may capture images of the brain of patient 104 for presentation on display 110. The movement of robotic arm 114 to place external scope 116 correctly over access port 106 may be guided by tracking system 112 and the computing device in equipment tower 108. The images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of the markers mentioned above).

Before a procedure such as that shown in FIG. 1 (which may be, for example, a tumor resection), preoperative images may be collected of patient 104, or at least of patient 104's brain or portions thereof. Such preoperative images may be collected using any of a variety of imaging modalities, such as Magnetic Resonance Imaging (MRI), Optical Coherence Tomography (OCT), ultrasound, Computed Tomography (CT), optical spectroscopy and the like. For each of the above-mentioned imaging modalities, various imaging techniques may be used. Polarization Sensitive OCT and OCT elastography are exemplary uses of the OCT modality. Diffusion MRI (also referred to as diffusion tensor imaging, DTI) is an example use of the MRI modality. Raman spectroscopy is an example use of optical spectroscopy. A variety of other examples of the above modalities will also occur to those skilled in the art.

Preoperative images may be used for planning purposes. During the procedure, additional images (referred to as intraoperative images) may be collected of the brain of patient 104, using any suitable ones of the above-mentioned modalities (it will be apparent to those skilled in the art that some imaging modalities are less suitable or unsuitable for preoperative use, while other imaging modalities are less suitable or unsuitable for intraoperative use).

An example of a planning activity that may be performed using preoperative images is the selection of entry locations and trajectories for surgical tools through the patient tissue (e.g., the brain of patient 104) to a target, such as a tumour to be resected. As will be apparent to those skilled in the art, surgical tools such as access port 106 may reach targeted areas via a wide variety of trajectories from the outer surface of the brain or other tissue. Some of those trajectories may be more suitable than others, for example due to reduced interference with cortical tissue, vascular tissue, or the like. As will be described in further detail below, the computing device housed in equipment tower 108 can perform various actions to process and render medical imaging data such as the above-mentioned preoperative images, selecting and implementing visual filters to distinguish between tissue types in the images.

Figure 2:
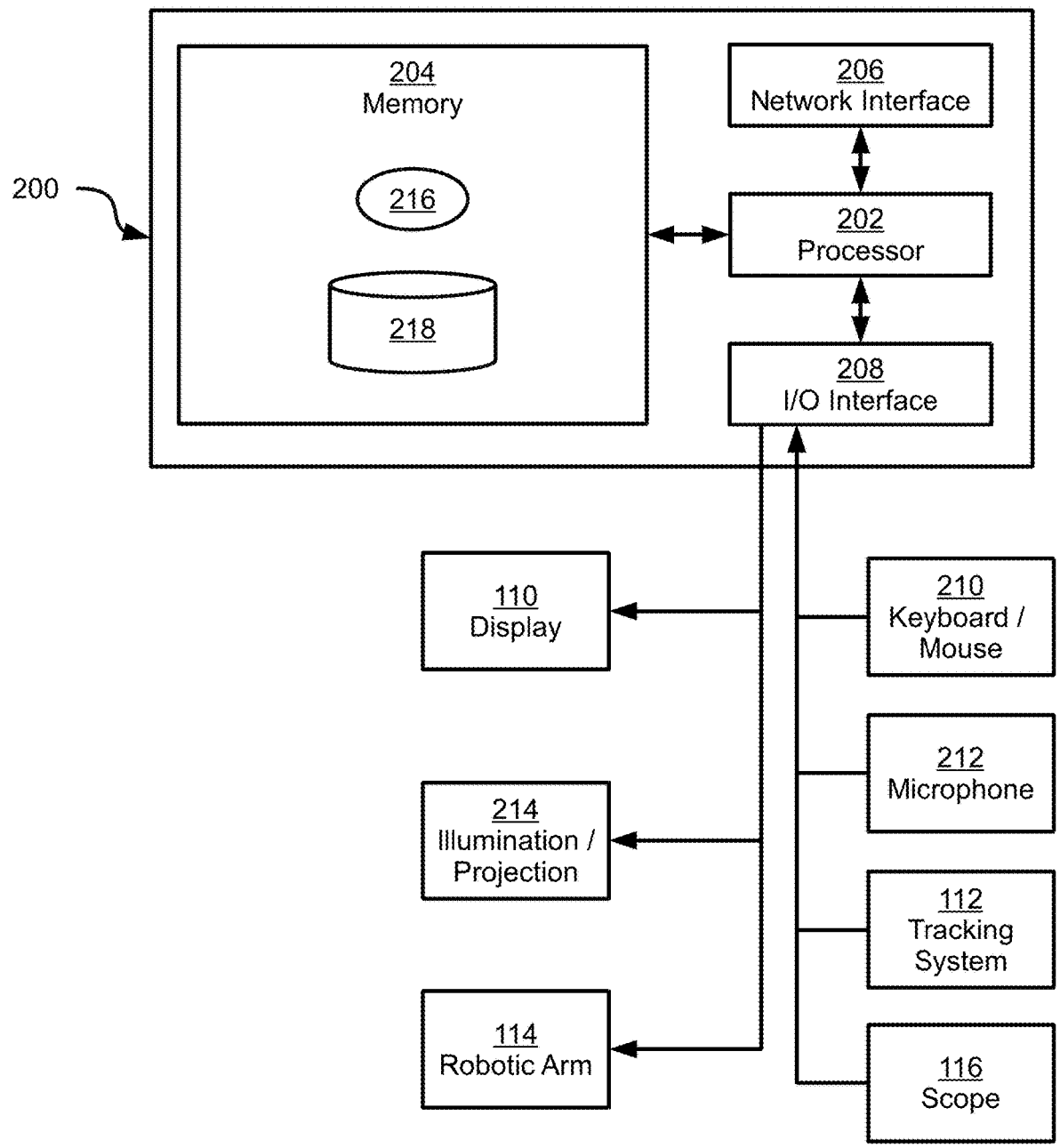
FIG. 2 depicts a computing device of the operating theatre of FIG. 1, according to a non-limiting embodiment.

Before a discussion of the functionality of the computing device, a brief description of the components of the computing device will be provided. Referring to FIG. 2, a computing device 200 is depicted, including a central processing unit (also referred to as a microprocessor or simply a processor) 202 interconnected with a non-transitory computer readable storage medium such as a memory 204.

Processor 202 and memory 204 are generally comprised of one or more integrated circuits (ICs), and can have a variety of structures, as will now occur to those skilled in the art (for example, more than one CPU can be provided). Memory 204 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 204 includes both a volatile memory and a non-volatile memory. Other types of non-transitory computer readable storage medium are also contemplated, such as compact discs (CD-ROM, CD-RW) and digital video discs (DVD).

Computing device 200 also includes a network interface 206 interconnected with processor 202. Network interface 206 allows computing device 200 to communicate with other computing devices via a network (e.g. a local area network (LAN), a wide area network (WAN) or any suitable combination thereof). Network interface 206 thus includes any necessary hardware for communicating over such networks, such as radios, network interface controllers (NICs) and the like.

Computing device 200 also includes an input/output interface 208, including the necessary hardware for interconnecting processor 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 208, computing device 200 is connected to input devices including a keyboard and mouse 210, a microphone 212, as well as scope 116 and tracking system 112, mentioned above. Also via interface 208, computing device 200 is connected to output devices including illumination or projection components 214 (e.g. lights, projectors and the like), as well as display 110 and robotic arm 114 mentioned above. Other input (e.g. touch screens) and output devices (e.g. speakers) will also occur to those skilled in the art.

It is contemplated that I/O interface 208 may be omitted entirely in some embodiments, or may be used to connect to only a subset of the devices mentioned above. The remaining devices may be connected to computing device 200 via network interface 206.

Computing device 200 stores, in memory 204, a rendering application 216 (also referred to herein as application 216) comprising a plurality of computer readable instructions executable by processor 202. When processor 202 executes the instructions of application 216 (or, indeed, any other application stored in memory 204), processor 202 performs various functions implemented by those instructions, as will be discussed below. Processor 202, or computing device 200 more generally, is therefore said to be "configured" or "operating" to perform those functions via the execution of application 216.

Also stored in memory 204 are various data repositories, including a patient data repository 218. Patient data repository 218 can contain a surgical plan defining the various steps of the minimally invasive surgical procedure to be conducted on patient 104, as well as image data relating to patient 104, such as MRI and CT scans, three-dimensional models of the brain of patient 104, and the like. In the present embodiment, repository 218 includes at least an image of a volume of patient tissue having an outer surface, such as the brain of patient 104.

Figure 3:
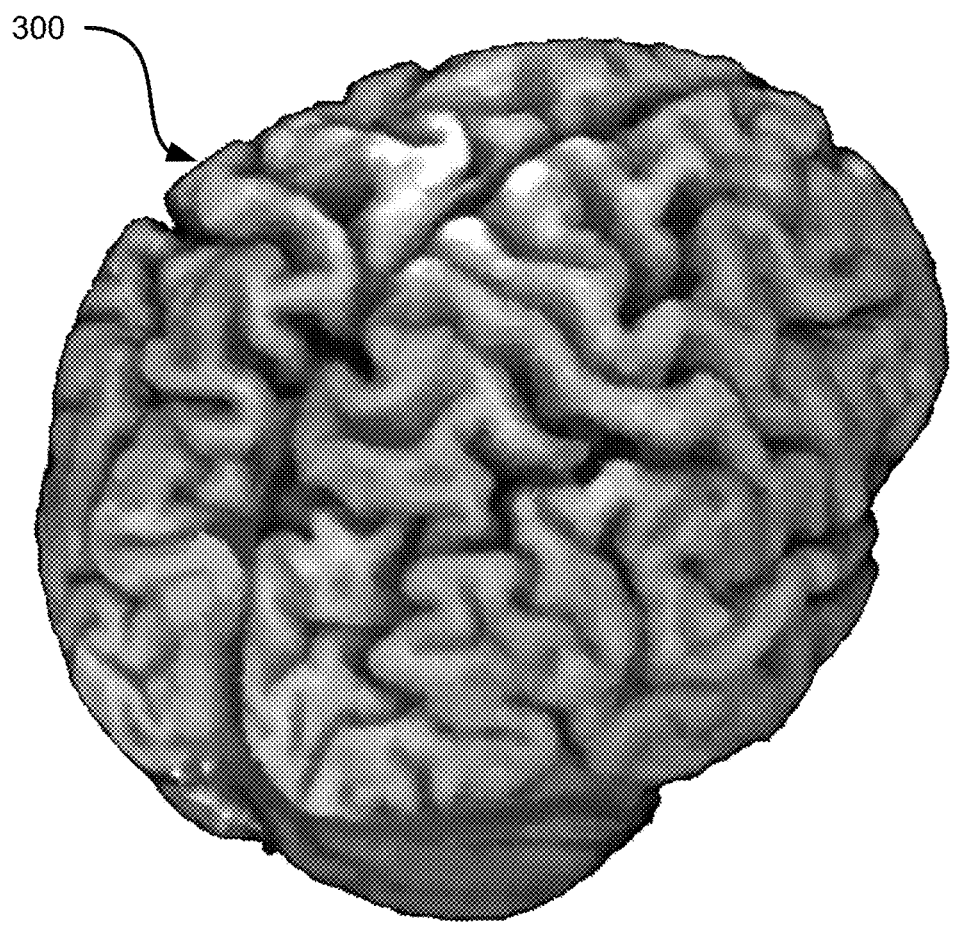
FIG. 3 depicts an image of a volume of tissue maintained by the computing device of FIG. 2, according to a non-limiting embodiment.

Referring to FIG. 3, an example image 300 of a volume of tissue stored in repository 218 is depicted. The volume of tissue is the brain of patient 104 in the present example, and image 300 is a three-dimensional image of the brain of patient 104 obtained via MRI scanning. As seen in FIG. 3, image 300 depicts an outer surface of the brain. Image 300 also includes image data depicting various internal structures of the brain (not visible in FIG. 3), and may further include image data depicting structures surrounding the brain (such as the skull of patient 104). In other words, the patient tissue depicted by the image 300 depicts a plurality of different tissue types.

Figure 4:
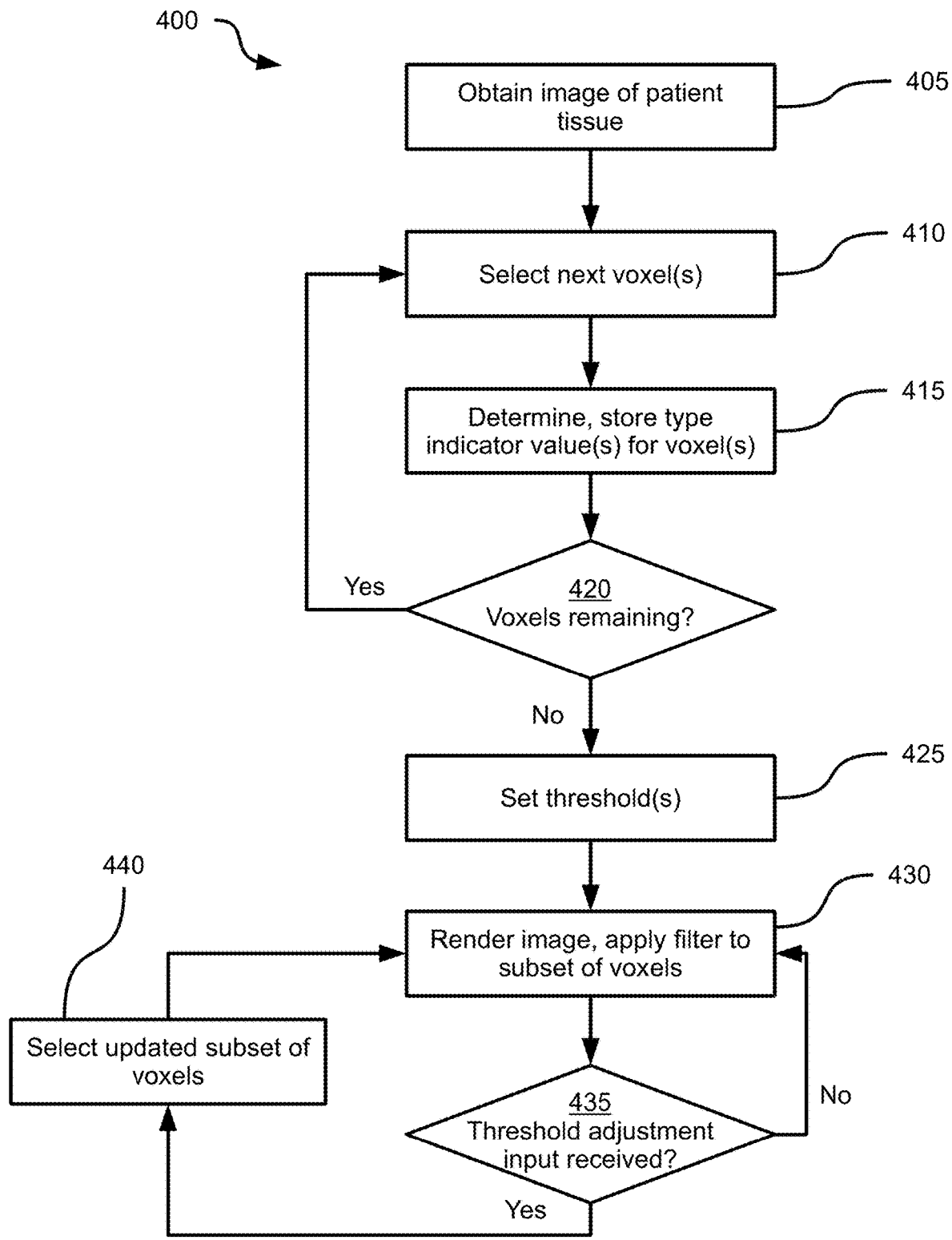
FIG. 4 depicts a method of rendering medical image data, according to a non-limiting embodiment.

Turning to FIG. 4, a method 400 of rendering medical image data is depicted. Method 400 will be discussed in connection with its performance in system 100, and particularly by the computing device 200, via the execution of application 216 by processor 202. As will be discussed in greater detail below, via the performance of method 400, computing device 200 is configured to render the image 300 and apply a variety of dynamically adjustable visual filters to distinguish various tissue types depicted in the image 300.

At block 405, the computing device 200 is configured to obtain an image of a volume of patient tissue having a plurality of tissue types. For example, at block 405 the processor 202 is configured to retrieve the image 300 from the memory 204 (e.g., from the repository 218), or to receive the image 300 from a medical imaging device such as an MR scanner. As will be apparent, the image 300 comprises a plurality of voxels, each defined by a location within the volume depicted by the image 300, and an intensity value (e.g., a greyscale intensity value between 0 and 255). The patient tissue depicted by the image 300 includes a plurality of tissue types. In the present example, in which the image 300 depicts a brain, the tissue types include any one or more of vascular tissue, grey matter nervous tissue, and white matter nervous tissue. In other examples, various other tissue types may also be depicted, including skin and bone tissues.

At block 410, the computing device 200 is configured to select one or more voxels to process. In some examples, each voxel is processed independently, while in other examples, groups of voxels are processed simultaneously.

At block 415, the computing device 200 is configured to determine and store at least a first type indicator value corresponding to each of the voxels selected at block 405. The type indicator value indicates a likelihood that the voxel depicts a particular tissue type. As noted above, the image 300 depicts a plurality of tissue types; at block 415, the computing device 200 can be configured to determine a plurality of type indicator values for each voxel selected at block 410, with each type indicator value indicating the likelihood that the selected voxel depicts the corresponding tissue type. Thus, in an example performance of block 415, the computing device 200 can be configured to determine and store first and second type indicator values for a given voxel, the first value indicating the likelihood that the voxel depicts a cortical surface, and the second value indicating the likelihood that the voxel depicts vascular tissue. As will now be apparent, additional type indicator values corresponding to additional tissue types can also be determined at block 415 for each voxel.

The nature of the determination of type indicator values is not particularly limited, and may depend on one or both of the imaging modality with which the image obtained at block 405 was captured, and the tissue type corresponding to the type indicator value. For example, the type indicator value may simply be the intensity value already stored for the selected voxel. Employing the intensity as the type indicator may be particularly effective with certain imaging modalities, such as CT. In other examples, the type indicator value is derived at least in part from the intensity of the voxel, but is not the intensity value itself. For example, the computing device 200 can be configured to determine a type indicator value corresponding to cortical surface tissue based not only on voxel intensity, but also on proximity of the voxel to previously recognized anatomical features (such as the skull of the patient, which may be identified in an earlier operation).

In a further example, probabilistic models may be applied to the voxel or voxels selected at block 410 to determine the type indicator values for those voxels. For example, the determination of type indicator values for vascular tissue can be performed by the computing device by assigning a probability to each voxel based on the intensity of that voxel in comparison to the intensities of surrounding voxels.

Having assigned a type indicator value (such as a likelihood between zero and one, or any other suitable indication of likelihood) to the voxel(s) selected at block 410, and stored the type indicator values in association with those voxels, the computing device 200 is configured to proceed to block 420. Various mechanisms for storing the type indicator values are contemplated. For example, the type indicator values computed for a given voxel can be stored in name-value pairs in the image 300 itself (e.g. in an additional field of each voxel). In other examples, the type indicator values are stored in a separate map, including a plurality of locations (each corresponding to the location of a given voxel in the image 300) and, for each location, one or more type indicator values. Where more than one type indicator values are determined at block 415, the type indicator values are also typically stored with an identifier of the corresponding tissue type (e.g. in a name-value pair as mentioned above).

At block 420, the computing device 200 is configured to determine whether any voxels in the image obtained at block 405 remain to be processed. When the determination at block 420 is affirmative, the performance of method 400 returns to block 410, at which the computing device 200 is configured to select the next voxel or set of voxels, and generate and store further type indicator values. The performance of blocks 410-420 is repeated until the determination at block 420 is negative. In other words, the computing device 200 is configured to determine a type indicator value for each voxel in the image obtained at block 405.

Following a negative determination at block 420, the computing device 200 proceeds to block 425. At block 425, the computing device 200 is configured to set an initial threshold value for the type indicator values determined at block 415. One threshold is set at block 425 for each type indicator determined at block 415. That is, if two type indicator values are determined at block 415 for each voxel (e.g., one type indicator value corresponding to cortical surface tissue, and another type indicator value corresponding to vascular tissue), two thresholds are set at block 425. For each type indicator, the threshold set at block 425 is a type indicator value selected between the highest and lowest voxel-specific type indicator values corresponding to a given type of tissue. The thresholds may be set in a variety of ways.

For example, in the case of tissue types for which the voxel intensities themselves are employed as type indicator values, the computing device 200 can be configured to set a threshold at block 425 as a predetermined intensity value. The intensity value may be selected previously based on empirical assessments of intensities typically observed for the relevant tissue type. In other examples, the threshold can be set by performing a thresholding operation on the voxels of the image 300, such as a Otsu-based clustering operation. In performing such an operation, the computing device 200 is configured to select an intensity value that divides the voxels into two classes, with one or both of maximal inter-class variation in intensities, and minimal intra-class variation in intensities.

In a further example, for probability-model based type indicator values, the computing device 200 can be configured to retrieve a default probability threshold (e.g. 50%) from the memory 204 and set the default probability threshold as the threshold at block 425.

When a plurality of distinct type indicator values have been determined for each voxel at block 415, the performance of block 425 may also include receiving a selection of tissue types for which to set thresholds. For example, the computing device 200 can present, on the display 110, a plurality of selectable elements each identifying one of the tissue types for which type indicator values were determined at block 415. The computing device 200 can be configured to receive input data (e.g., via the keyboard and mouse 210 or any other suitable input device) selecting one or more of the above-mentioned selectable elements. The selection received from the input device indicates which tissue types to identify in a rendering of the image obtained at block 405, via the application of visual filters, as discussed below. The computing device 200 can further be configured to generate thresholds only for those tissue types that have been selected. In other examples, however, the computing device 200 is configured to set a threshold for each tissue type and store the threshold in the memory 204, whether or not the tissue type has been selected for display.

At block 430, having set one or more thresholds, the computing device 200 is configured to render the image obtained at block 405, and apply at least a first visual filter to a subset of the voxels with type indicator values that satisfy the threshold set at block 425. That is, the computing device 200 is configured to identify the subset of voxels in the image 300 with, for example, an intensity that exceeds the intensity specified by the threshold set at block 425. The computing device 200 is further configured, upon rendering the image 300 on the display 110, to apply a visual filter to the above-mentioned subset of voxels in order to visually distinguish those voxels from the voxels that do not satisfy the threshold.

The visual filter may be, for example, the application of a colour to each voxel in the subset (where the voxels outside the subset may be displayed in grayscale). In other examples, the visual filter includes rendering the voxels within the subset with a first opacity, and the voxels outside the subset with a second opacity different from the first opacity.

Figure 5:
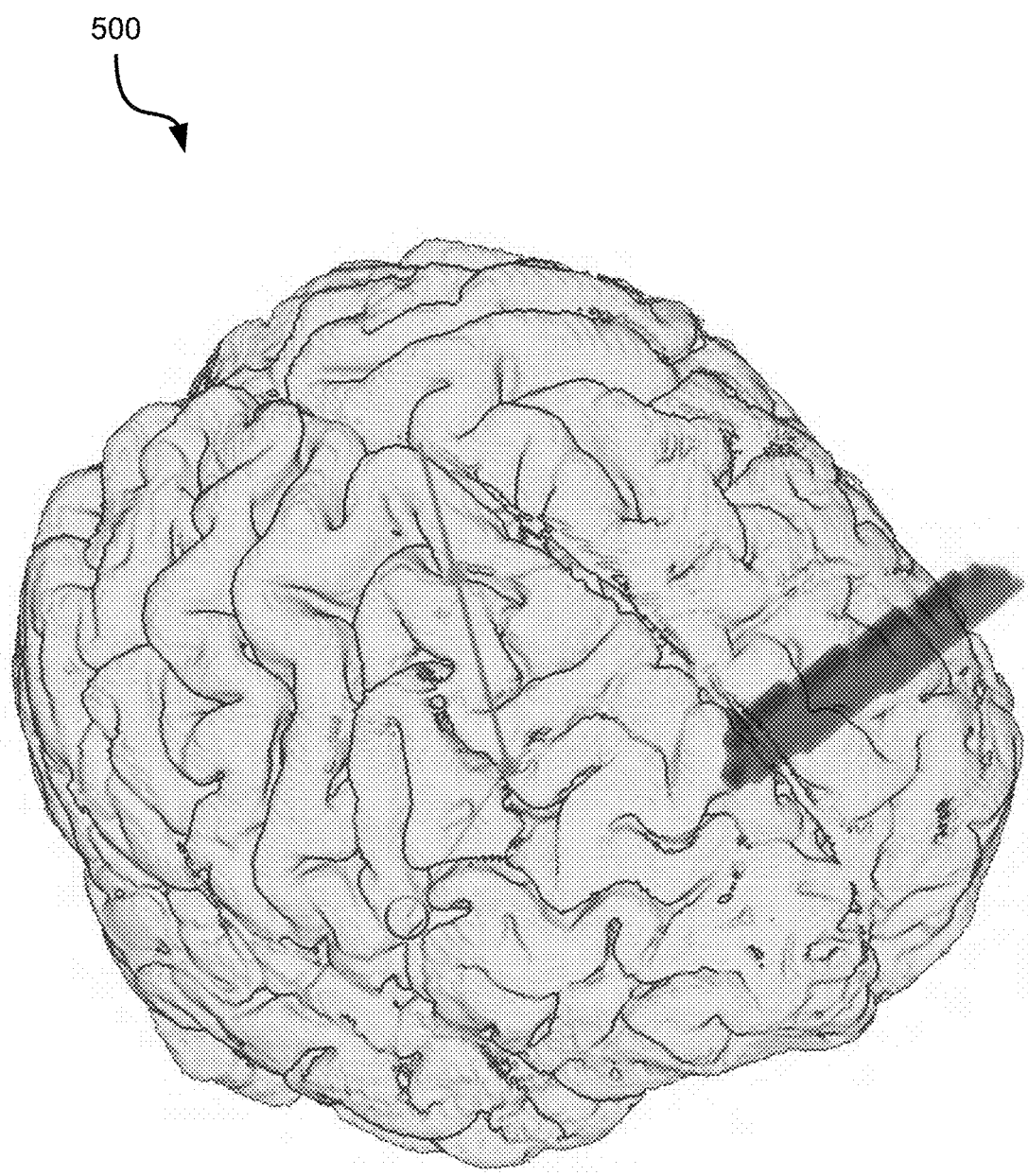
FIGS. 5-6 depict a set of renderings produced via the method of FIG. 4.

Turning to FIG. 5, a rendering 500 resulting from an example performance of block 430 is illustrated, in which a visual filter has been applied to voxels satisfying a cortical surface tissue threshold. Thus, each voxel having a type indicator value that indicates a sufficient likelihood (i.e. a likelihood greater than that specified by the threshold) that the voxel depicts the cortical surface is rendered with a predefined colour, opacity, and the like.

Returning to FIG. 4, at block 435, the computing device 200 is configured to determine whether a threshold adjustment input has been received. The threshold adjustment input includes input data received at the processor 202 from an input device such as the keyboard and mouse 210 and specifying a change to the threshold set at block 425. When the determination at block 435 is negative, the computing device 200 continues to render the image with the initial visual filter. When, however, the determination at block 430 is affirmative, the computing device 200 proceeds to block 440 to select an updated subset of voxels based on the adjusted threshold, and returns to block 430.

Figure 6:
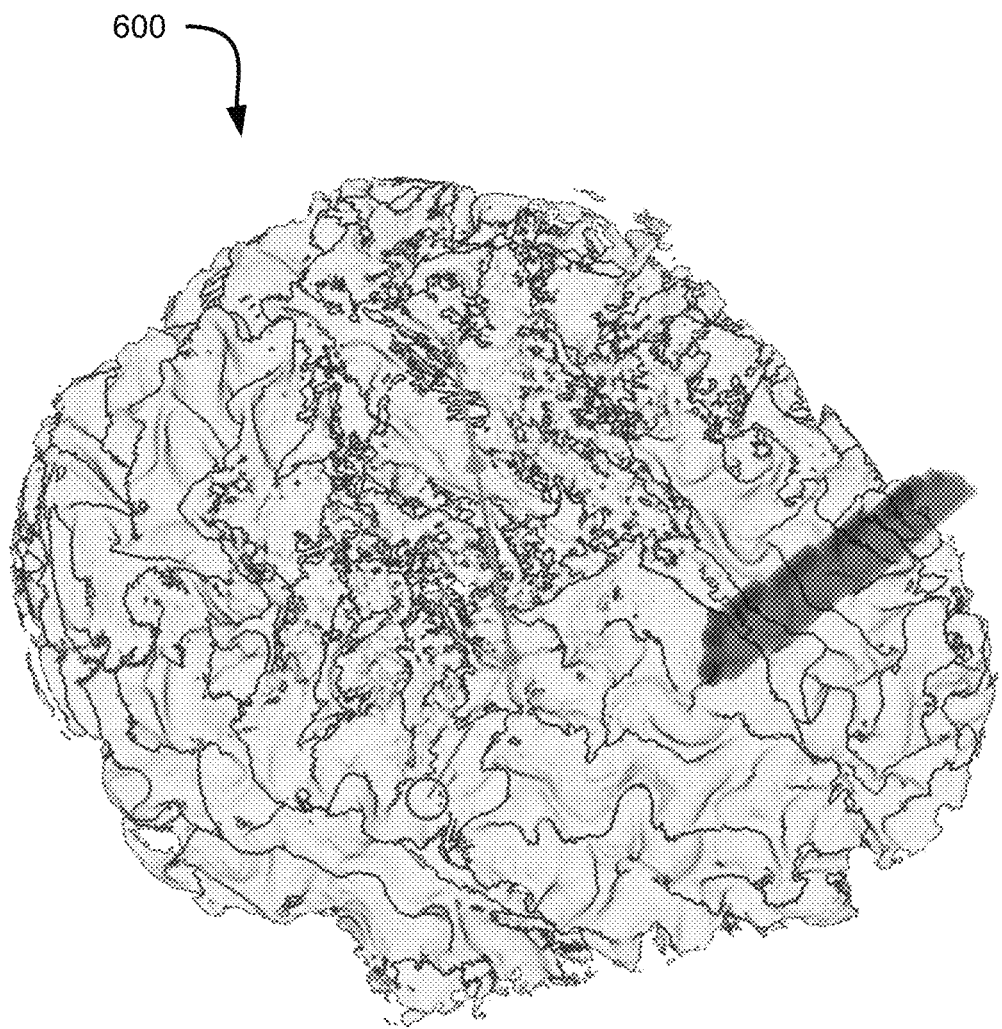
Figure 6:
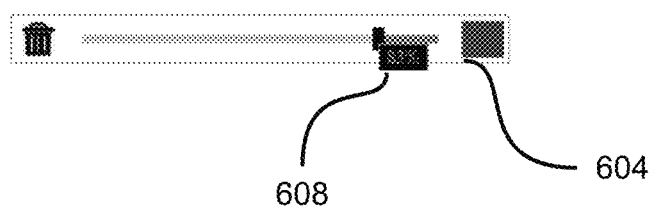

For example, turning to FIG. 6, a rendering 600 is shown, in which a threshold adjustment interface element 604, including a selectable slider 608, is shown on the display 110. The slider 608 is selectable to specify adjustments to the threshold applied to cortical surface type indicator values. While the rendering 500 of FIG. 5 applied the visual filter to a subset of voxels having at least a 50% likelihood of representing cortical surface tissue, the slider 608 has been manipulated in the rendering 600 to adjust the threshold from 50% to 83%. As a result, the computing device 200 is configured to apply the above-mentioned visual filter to an updated subset of voxels. As seen from a comparison of FIGS. 5 and 6, the updated subset of voxels contains a smaller number of voxels than the initial subset of voxels.

A wide variety of threshold adjustment mechanisms other than the element 604 and the slider 608 are contemplated. For example, the threshold adjustment may be specified by numerical or text input, or via any of a variety of other selectable interface elements presented on the display 110.

Figure 7:
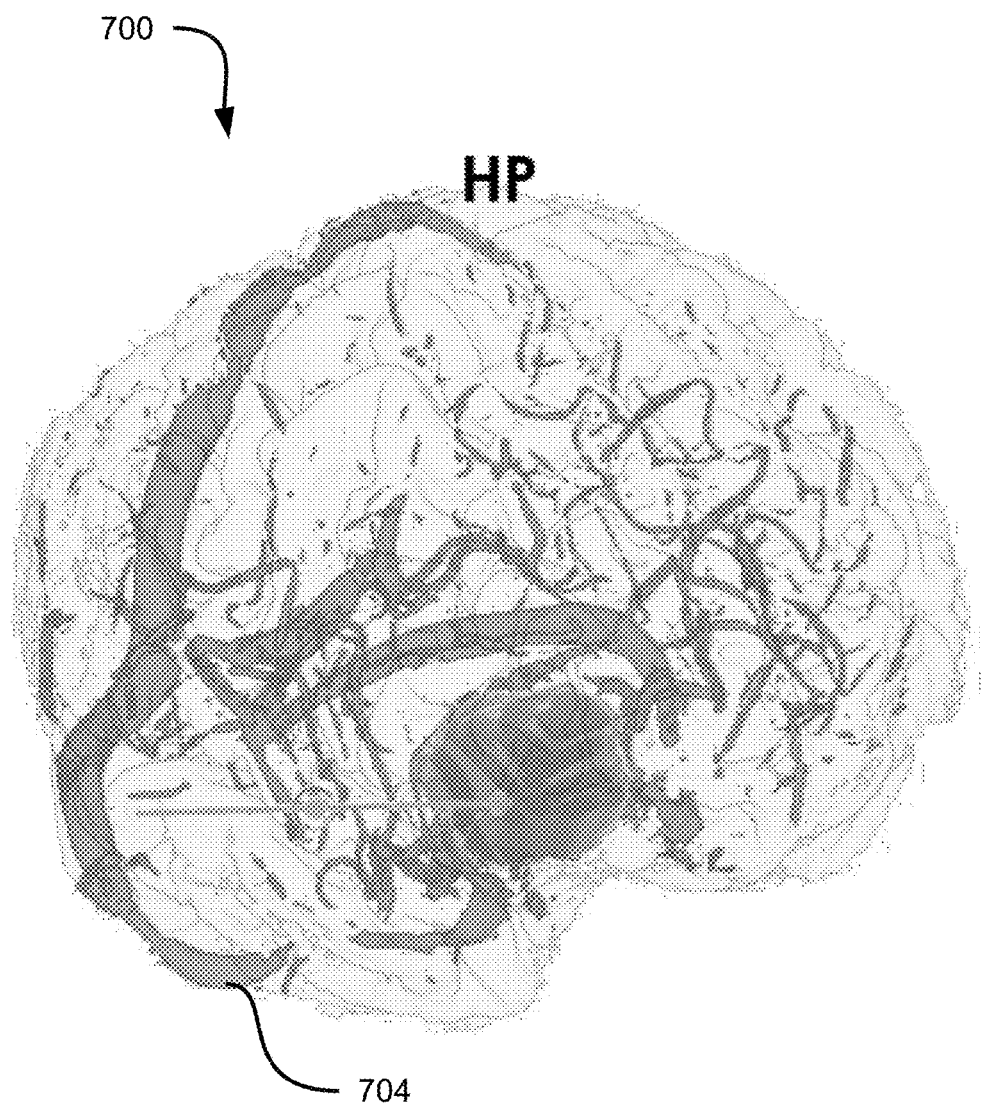
FIGS. 7-9 depict a further set of renderings produced via the method of FIG. 4
Figure 8:
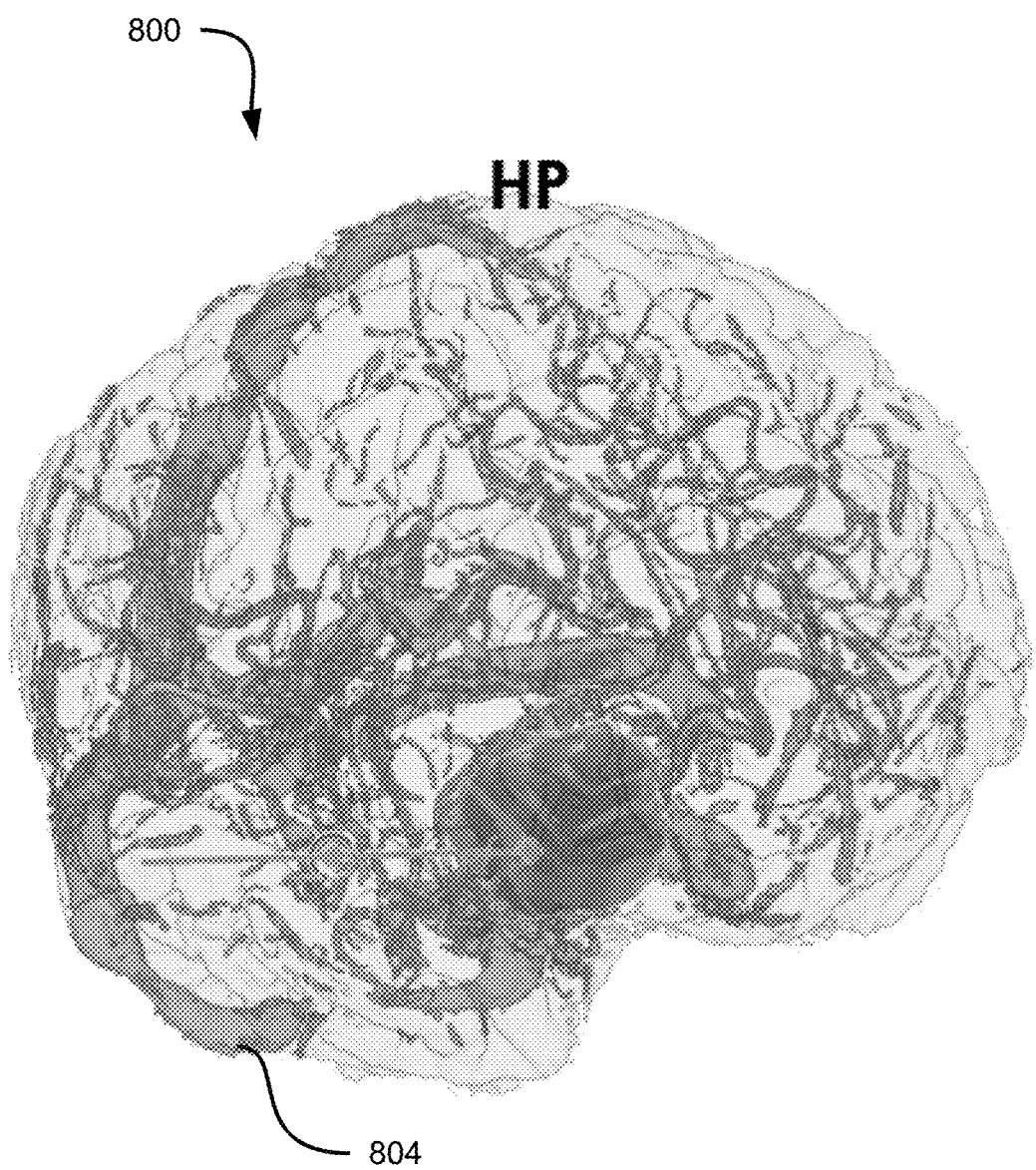
Figure 9:
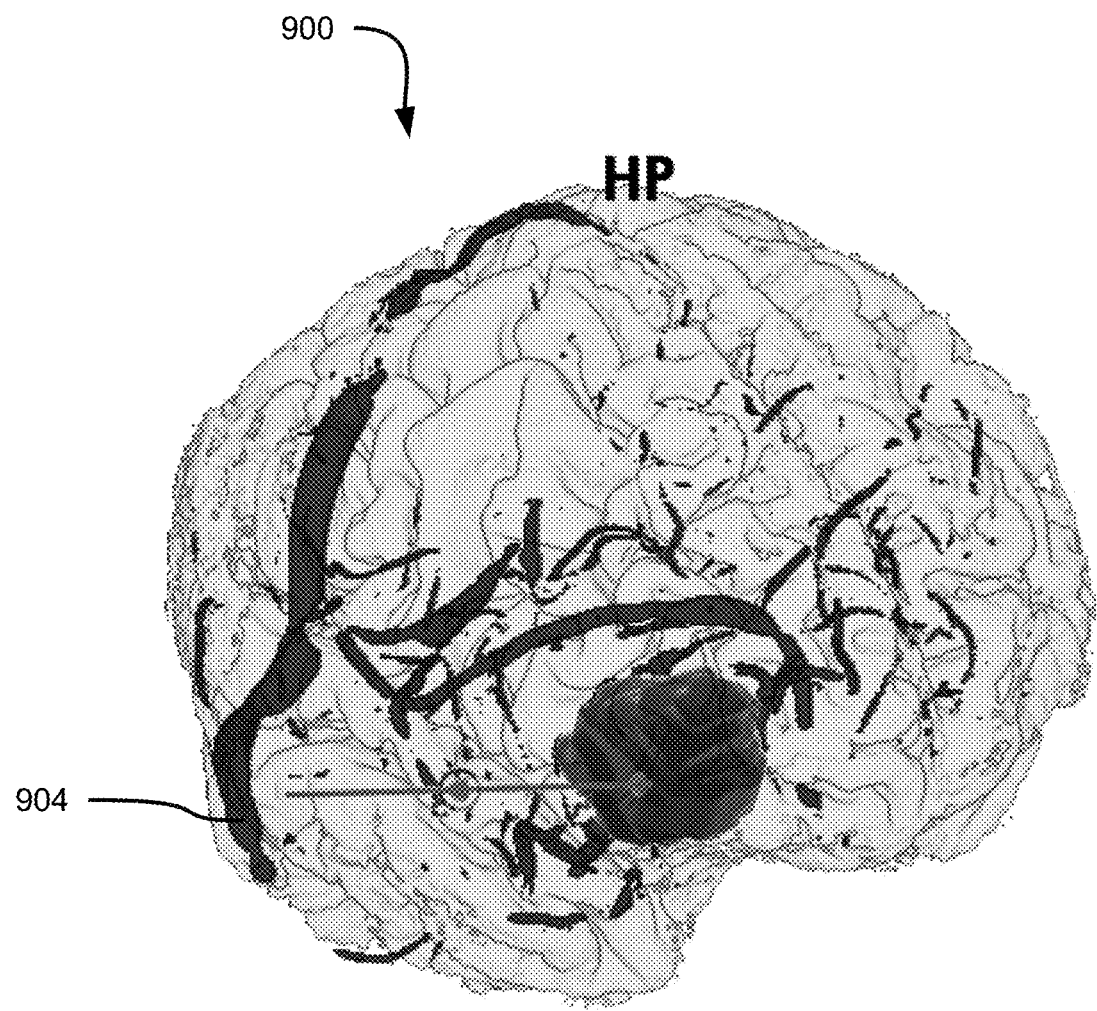

FIGS. 7-9 depict, respectively, renderings 700, 800 and 900 illustrating threshold adjustments for vascular tissue rather than the cortical surface tissue illustrated in FIGS. 5-6. As seen in FIG. 7, the threshold set at block 425 results in an initial subset 704 being rendered with a visual filter. In particular, the filter shown in FIG. 7 includes the application of a color to the subset of voxels, as well as the application of a greater opacity to the subset of voxels than to those voxels that are not members of the subset.

FIGS. 8 and 9 illustrate renderings 800 and 900, in which updated subsets of voxels 804 and 904 have been selected and visually filtered following adjustments to the threshold initially applied in the rendering 700. In particular, the rendering 800 illustrates an adjustment lowering the threshold and therefore applying the visual filter to a larger subset of voxels. The rendering 900, meanwhile, illustrates an adjustment raising the threshold (i.e., requiring a greater probability of each voxel in the subset depicting vascular tissue) and therefore applying the visual filter to a smaller subset of voxels.

As will now be apparent, the computing device 200 can be configured to render the image with a plurality of different visual filters applied to a corresponding plurality of voxel subsets. For example, the computing device 200 can render the image 300 and apply a first visual filter to a first subset of voxels depicting cortical surface tissue, as well as apply a second visual filter to a second subset of voxels depicting vascular tissue. Further, the computing device 200 is configured, when rendering the image with multiple visual filters, to determine whether any of the voxels in the image satisfy more than one of the set of thresholds applied for the rendering. When the determination is affirmative, the computing device 200 is configured to select a single one of the subsets in which to place the voxel. For example, the computing device 200 may be configured to place the voxel in the subset corresponding to the tissue type for which the voxel has the greatest type indicator value (that is, the greatest likelihood of depicting the corresponding tissue type).

Those skilled in the art will appreciate that in some embodiments, the functionality of the application 216 may be implemented using pre-programmed hardware or firmware elements (e.g., application specific integrated circuits (ASICs), electrically erasable programmable read-only memories (EEPROMs), etc.), or other related components.

The scope of the claims should not be limited by the embodiments set forth in the above examples, but should be given the broadest interpretation consistent with the description as a whole.

The invention claimed is:

1. A method of rendering medical image data, comprising:
obtaining an image of a volume of patient tissue having a plurality of tissue types; the image comprising a plurality of voxels;
for each of the plurality of voxels:
determining a first type indicator value indicating a likelihood that the voxel depicts a first one of the tissue types; and
storing the first type indicator value in association with the voxel;
setting a first type indicator threshold for the first tissue type;
rendering the image on a display and applying a first visual filter to a first subset of the voxels having type indicator values that satisfy the first type indicator threshold;
rendering, on the display with the image, a selectable threshold adjustment element;
receiving input data via selection of the threshold adjustment element, the input data defining a modified first type indicator threshold; and
updating the rendering, responsive to receiving the input data, to apply the first visual filter to an updated first subset of the voxels having first type indicator values that satisfy the modified first type indicator threshold.

2. The method of claim 1, further comprising:
for each of the plurality of voxels:
determining a second type indicator value indicating a likelihood that the voxel depicts a second one of the tissue types;
storing the second type indicator value in association with the voxel; and setting a second type indicator threshold for the second tissue type.

3. The method of claim 2, wherein the rendering further comprises applying a second visual filter to a second subset of the voxels having second type indicators that satisfy the second type indicator threshold.

4. The method of claim 3, wherein the rendering further comprises:
when a voxel is a member of the first subset and the second subset, determining whether the corresponding first and second type indicator values satisfy the respective type indicator thresholds; and
when the determination is affirmative, selecting one of the first and second visual filters to apply to the voxel.

5. The method of claim 1, wherein determining the first type indicator value comprises executing a probability model based on the intensity of the voxel and the intensity of adjacent voxels.

6. The method of claim 1, wherein the first type indicator value is an intensity value of the voxel.

7. The method of claim 1, wherein the plurality of tissue types includes one or more of vascular tissue and nervous tissue.

8. The method of claim 1, wherein the plurality of tissue types includes one or more of vascular tissue, grey matter nervous tissue, and white matter nervous tissue.

9. A computing device for rendering medical image data, comprising:
an input device;
a display;
a memory;
a processor interconnected with the input device, the display and the memory, the processor configured to;
obtain, from the memory, an image of a volume of patient tissue having a plurality of tissue types; the image comprising a plurality of voxels;
for each of the plurality of voxels:
determine a first type indicator value indicating a likelihood that the voxel depicts a first one of the tissue types; and
store the first type indicator value in association with the voxel;
set a first type indicator threshold for the first tissue type;
render the image on the display and apply a first visual filter to a first subset of the voxels having type indicator values that satisfy the first type indicator threshold;
render, on the display with the image, a selectable threshold adjustment element;
receive input data via selection of the threshold adjustment element at the input the device, the input data defining a modified first type indicator threshold; and
update the rendering, responsive to receiving input data via the input device specifying a modified first type indicator threshold, to apply the first visual filter to an updated first subset of the voxels having first type indicator values that satisfy the modified first type indicator threshold.

10. The computing device of claim 9, the processor further configured to:
for each of the plurality of voxels:
determine a second type indicator value indicating a likelihood that the voxel depicts a second one of the tissue types;
store the second type indicator value in association with the voxel; and
set a second type indicator threshold for the second tissue type.

11. The computing device of claim 10, the processor further configured to render the image by: applying a second visual filter to a second subset of the voxels having second type indicators that satisfy the second type indicator threshold.

12. The computing device of claim 11, the processor further configured to render the image by:
when a voxel is a member of the first subset and the second subset, determining whether the corresponding first and second type indicator values satisfy the respective type indicator thresholds; and
when the determination is affirmative, selecting one of the first and second visual filters to apply to the voxel.

13. The computing device of claim 9, the processor further configured to determine the first type indicator value by executing a probability model based on the intensity of the voxel and the intensity of adjacent voxels.

14. The computing device of claim 9, wherein the first type indicator value is an intensity value of the voxel.

15. The computing device of claim 9, wherein the plurality of tissue types includes one or more of vascular tissue and nervous tissue.

16. The computing device of claim 9, wherein the plurality of tissue types includes one or more of vascular tissue, grey matter nervous tissue, and white matter nervous tissue.

* * * * *